United States Patent
Cannell et al.

(10) Patent No.: US 7,696,140 B2
(45) Date of Patent: Apr. 13, 2010

(54) COMPOSITION CONTAINING A PHOSPHOLIPID AND QUATERNARY AMMONIUM POLYMER

(75) Inventors: David W. Cannell, Plainfield, NJ (US); Jean-Marc Ascione, Paris (FR); Julio Toucet, New York, NY (US)

(73) Assignee: L'Oreal S.A., Paris (FR)

(*) Notice: Subject to any disclaimer, the term of this patent is extended or adjusted under 35 U.S.C. 154(b) by 150 days.

(21) Appl. No.: 11/542,213

(22) Filed: Oct. 4, 2006

(65) Prior Publication Data

US 2008/0085849 A1   Apr. 10, 2008

(51) Int. Cl.
*C11D 1/94* (2006.01)
*C11D 3/36* (2006.01)
*C11D 3/37* (2006.01)

(52) U.S. Cl. ........... 510/122; 510/119; 510/123; 510/130; 510/150; 510/155; 510/413; 510/422; 510/432; 510/467; 510/468

(58) Field of Classification Search ........... 510/119, 510/123, 130, 122, 150, 155, 413, 422, 432, 510/467, 468
See application file for complete search history.

(56) References Cited

U.S. PATENT DOCUMENTS

| | | | | |
|---|---|---|---|---|
| 5,393,452 | A | * | 2/1995 | Raleigh et al. ......... 424/70.121 |
| 5,449,475 | A | * | 9/1995 | Cauwet et al. ........... 424/70.13 |
| 5,658,651 | A | * | 8/1997 | Smith et al. ................... 442/59 |
| 5,876,705 | A | * | 3/1999 | Uchiyama et al. ........ 424/70.12 |
| 6,015,574 | A | * | 1/2000 | Cannell et al. .............. 424/450 |
| 6,221,389 | B1 | * | 4/2001 | Cannell et al. .............. 424/450 |
| 6,524,614 | B2 | | 2/2003 | Cannell et al. |
| 6,558,697 | B2 | | 5/2003 | Cannell et al. |
| 6,660,045 | B1 | * | 12/2003 | Hoeffkes et al. ............... 8/405 |
| 2004/0120919 | A1 | | 6/2004 | Nguyen et al. |

\* cited by examiner

*Primary Examiner*—Charles I Boyer
(74) *Attorney, Agent, or Firm*—Oblon, Spivak, McClelland, Maier & Neustadt, L.L.P.

(57) ABSTRACT

The invention relates to compositions containing at least one alcohol-insoluble quaternary ammonium polymer, at least one amphoteric surfactant, at least one nonionic surfactant and, optionally, at least one phospholipid compound as well as to methods of using and preparing such compositions.

10 Claims, No Drawings

COMPOSITION CONTAINING A PHOSPHOLIPID AND QUATERNARY AMMONIUM POLYMER

FIELD OF THE INVENTION

The present invention generally relates to compositions comprising quaternary ammonium polymers as well as to methods of applying such compositions to keratin materials and to methods of preparing such compositions. Such compositions possess improved properties and characteristics such as, for example, providing increased conditioning, strengthening and/or disentangling to keratin materials (for example, hair).

BACKGROUND OF THE INVENTION

Including alcohol-insoluble quaternary ammonium polymers in alcohol-containing compositions can be problematic given their solubility limitations. Given that many hair compositions contain significant amounts of alcohol, adding alcohol-insoluble quaternary ammonium polymers to such compositions can be difficult and/or can result in a composition in which some or much of the alcohol-insoluble quaternary ammonium polymers are inactive.

Thus, there is a need for improved alcohol-insoluble quaternary ammonium polymers-containing compositions in which much or all of the alcohol-insoluble quaternary ammonium polymers remain active, particularly alcohol-containing compositions.

Accordingly, one aspect of the present invention is a care and/or coloring and/or treatment composition for keratin materials such as hair which is able to address or overcome some or all of the aforementioned problems with the prior art compositions.

SUMMARY OF THE INVENTION

The present invention relates to compositions, particularly cosmetic compositions for hair such as shampoos and conditioners, comprising (a) at least one alcohol-insoluble quaternary ammonium polymer; (b) at least one amphoteric surfactant; and (c) at least one nonionic surfactant.

The present invention also relates to compositions, particularly cosmetic compositions for hair such as shampoos and conditioners, comprising (a) at least one alcohol-insoluble quaternary ammonium polymer; (b) at least one amphoteric surfactant; (c) at least one nonionic surfactant; and (d) at least one phospholipid compound.

The present invention also relates to methods of at least one alcohol-insoluble quaternary ammonium polymer comprising combining the at least one alcohol-insoluble quaternary ammonium polymer with at least one amphoteric surfactant and at least one nonionic surfactant. Preferably, the at least one alcohol-insoluble quaternary ammonium polymer is also combined with a phospholipid compound.

The present invention further relates to methods of producing a composition comprising at least one alcohol-insoluble quaternary ammonium polymer comprising combining the at least one alcohol-insoluble quaternary ammonium polymer with at least one amphoteric surfactant and at least one nonionic surfactant. Preferably, the at least one alcohol-insoluble quaternary ammonium polymer is also combined with a phospholipid compound.

The present invention also relates to methods of conditioning, strengthening and/or disentangling hair comprising applying a composition comprising at least one alcohol-insoluble quaternary ammonium polymer, at least one amphoteric surfactant and at least one nonionic surfactant to the hair in an amount sufficient to condition, strengthen and/or disentangle the hair. Preferably, the composition also comprises a phospholipid compound.

The present invention also relates to methods of treating, caring for and/or enhancing the appearance of keratin materials comprising applying compositions of the present invention to the keratin materials in an amount sufficient to treat, care for and/or enhance the appearance of the keratin materials.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

"Cosmetically acceptable" means that the item in question is compatible with any keratin material. For example, "cosmetically acceptable medium" means a medium that is compatible with any keratin material.

"Keratin material" includes, for example, skin, hair, nails, eyelashes, eyebrows, eyelids, lips and any other area of body or facial skin.

The compositions, methods and kits of the present invention can comprise, consist of, or consist essentially of the essential elements and limitations of the invention described herein, as well as any additional or optional ingredients, components, or limitations described herein or any otherwise useful ingredient found in personal care compositions intended for application to keratin materials.

The composition of the present invention may be in any form suitable for use on keratin materials such as, for example, non-solid anhydrous, oil-free or emulsion compositions (for example, water-in-oil emulsion, oil-in-water emulsion, multiple emulsion (W/O/W or O/W/O), nanoemulsions, etc.). The compositions of the present invention can be, for example, shampoos, leave-in conditioners, rinse-out conditioners, hair styling compositions, hair coloring compositions, etc.

As defined herein, stability is tested by placing the composition in a controlled environment chamber for 8 weeks at 25° C. In this test, the physical condition of the sample is inspected as it is placed in the chamber. The sample is then inspected again at 24 hours, 3 days, 1 week, 2 weeks, 4 weeks and 8 weeks. At each inspection, the sample is examined for abnormalities in the composition such as phase separation if the composition is in the form of an emulsion. The stability is further tested by repeating the 8-week test at 25° C., 37° C., 45° C. and/or under freeze-thaw conditions. A composition is considered to lack stability if in any of these tests an abnormality that impedes functioning of the composition is observed. The skilled artisan will readily recognize an abnormality that impedes functioning of a composition based on the intended application.

Alcohol-Insoluble Quaternary Ammonium Polymer

According to the present invention, compositions comprising at least one alcohol-insoluble quaternary ammonium polymer are provided. The at least one alcohol-insoluble quaternary ammonium polymer is a polymer comprising alkyl-substitued diamine monomers. For example, the alcohol-insoluble quaternary ammonium polymer is preferably a polymer comprising repeating units of formula (a):

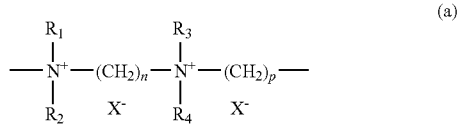

wherein:

$R_1$, $R_2$, $R_3$ and $R_4$, which may be identical or different, are each chosen from alkyl groups comprising from 1 to 4 carbon atoms and hydroxyalkyl groups comprising from 1 to 4 carbon atoms;

n and p, which may be identical or different, are each chosen from integers ranging from 2 to 20; and $X^-$ is an anion chosen from anions derived from inorganic acids and anions derived from organic acids.

Representative polymers of formula (a) include those in which $R_1$, $R_2$, $R_3$ and $R_4$ are chosen from methyl and ethyl groups and $X^-$ is a halogen atom such as a halogen chosen from chlorine, iodine and bromine.

Further, representative polymers of formula (a) include polymers in which $R_1$, $R_2$, $R_3$ and $R_4$ are methyl groups and n=3, p=6 and X=Cl, such as those of which the molecular weight, determined by gel-permeation chromatography, ranges from 9500 to 9900 and exemplified by formula (W):

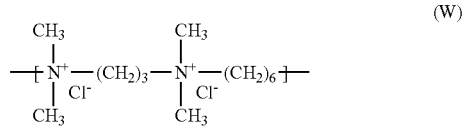

Other polymers of formula (a) include those where $R_1$ and $R_2$ are methyl groups, $R_3$ and $R_4$ are ethyl groups and n=p=3 and X=Br, such as those of which the molecular weight, determined by gel-permeation chromatography, is approximately 1200 and exemplified by formula (U):

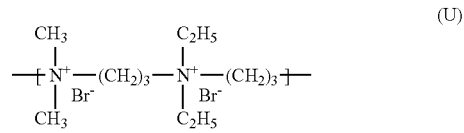

Such quaternary ammonium polymers of formula (a) can be prepared as described in French Patent 2,270,846, the disclosure of which is incorporated by reference herein.

Particularly preferred examples of the at least one alcohol-insoluble quaternary ammonium polymer are polyquaternium-34 and Ionene G, also known as hexadimethrine chloride, which is a polymer of N,N,N',N'-tetramethylhexamethylenediamine and trimethylene chloride and is disclosed in U.S. patent application publication No. 2002/0013972, the entire contents of which is hereby incorporated by reference.

Preferably, the at least one alcohol-insoluble quaternary ammonium polymer is present in an amount of at least 0.5%, more preferably at least 0.75%, more preferably at least 1.0%, and more preferably at least 1.1% by weight with respect to the total weight of the composition. Preferred ranges are from about 0.4% to about 1.25% by weight of the total weight of the composition, more preferably from about 0.8% to about 1.20% of the total weight of the composition, more preferably from about 0.8% to about 1.1% of the total weight of the composition, and most preferably from about 0.85% to about 1.05%, including all ranges and subranges therebetween.

Amphoteric Surfactant

According to the present invention, compositions comprising at least one amphoteric surfactant are provided. Any amphoteric surfactant(s) can be used in accordance with the present invention. Suitable amphoteric surfactants include, but are not limited to, betaines, sultaines, hydroxysultaines, alkyl amphodiacetates, alkyl amphodipropionates, and imidazolines, including salts of these compounds. Other suitable amphoteric surfactants include other fatty acid condensates such as those formed with amino acids, proteins, and the like.

Specific examples of acceptable amphoteric surfactants include cocamphodipropionates (for example, MIRANOL C2M-SF Conc. (disodium cocamphodipropionate) available from Rhne-Poulenc), CROSULTAINE C-50 (cocamidopropyl hydroxysultaine) available from Croda, disodium wheatgermimido PEG-2 sulfosuccinate available under the trade name MACKANATE WGD from Mcintyre Group Ltd, and disodium soyamphodiacetate available under the trade name MACKAM 2S from Mcintyre Group Ltd.

Preferably, the amphoteric surfactant(s) is/are present in an amount ranging from about 1% to about 20% by weight of the total weight of the composition, more preferably from about 1% to about 10% of the total weight of the composition, more preferably from about 2% to about 8% of the total weight of the composition, and most preferably from about 3% to about 7%, including all ranges and subranges therebetween. Often, amphoteric surfactants are available in commercial products which also contain a solvent or carrier, meaning that the commercial products contain a "% active material" of the amphoteric surfactant. It is to be understood that the above percentages refer to such % active materials. In a preferred embodiment, the Ionene G and the amphoteric surfactant(s) are present in a ratio of from about 1:1 to about 1:2.

Nonionic Surfactant

According to the present invention, compositions comprising at least one nonionic surfactant are provided. Any nonionic surfactant(s) can be used in accordance with the present invention.

In general, nonionic surfactants having a Hydrophilic-Lipophilic Balance (HLB) of 8 or more, preferably from 8 to 20, are contemplated for use by the present invention. Nonlimiting examples of nonionic surfactants useful in the compositions of the present invention are disclosed in McCutcheon's "Detergents and Emulsifiers," North American Edition (1986), published by Allured Publishing Corporation; and McCutcheon's "Functional Materials," North American Edition (1992); both of which are incorporated by reference herein in their entirety.

Examples of nonionic surfactants useful herein include, but are not limited to, alkoxylated derivatives of the following: fatty alcohols, alkyl phenols, fatty acids, fatty acid esters and fatty acid amides, wherein the alkyl chain is in the C12-C50 range, preferably in the C16-C40 range, more preferably in the C24 to C40 range, and having from about 1 to about 110 alkoxy groups. The alkoxy groups are selected from the group consisting of C2-C6 oxides and their mixtures, with ethylene oxide, propylene oxide, and their mixtures being the preferred alkoxides. The alkyl chain may be linear, branched, saturated, or unsaturated. Of these alkoxylated non-ionic surfactants, the alkoxylated alcohols are preferred, and the ethoxylated alcohols and propoxylated alcohols are more preferred. The alkoxylated alcohols may be used alone or in mixtures thereof. The alkoxylated alcohols may also be used in mixtures with those alkoxylated materials disclosed herein-above.

Other representative examples of such ethoxylated fatty alcohols include laureth-3 (a lauryl ethoxylate having an average degree of ethoxylation of 3), laureth-23 (a lauryl ethoxylate having an average degree of ethoxylation of 23), ceteth-10 (a cetyl alcohol ethoxylate having an average degree of ethoxylation of 10) steareth-100 (a stearyl alcohol ethoxylate having an average degree of ethoxylation of 10), and steareth-2 (a stearyl alcohol ethoxylate having an average degree of ethoxylation of 2), steareth-100 (a stearyl alcohol ethoxylate having an average degree of ethoxylation of 100), beheneth-5 (a behenyl alcohol ethoxylate having an average degree of ethoxylation of 5), beheneth-10 (a behenyl alcohol ethoxylate having an average degree of ethoxylation of 10), and other derivatives and mixtures of the preceding.

Also available commercially are Brij® nonionic surfactants from Uniqema, Paterson, N.J. Typically, Brij® is the condensation products of aliphatic alcohols with from about 1 to about 54 moles of ethylene oxide, the alkyl chain of the alcohol being typically a linear chain and having from about 8 to about 22 carbon atoms, for example, Brij 72 (i.e., Steareth-2) and Brij 76 (i.e., Steareth-10).

Also useful herein as nonionic surfactants are alkyl glycosides, which are the condensation products of long chain alcohols, e.g. C8-30 alcohols, with sugar or starch polymers. These compounds can be represented by the formula $(S)n-O-R$ wherein S is a sugar moiety such as glucose, fructose, mannose, galactose, and the like; n is an integer of from about 1 to about 1000, and R is a C8-30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants are alkyl polyglucosides wherein S is a glucose moiety, R is a C8-20 alkyl group, and n is an integer of from about 1 to about 9. Commercially available examples of these surfactants include decyl polyglucoside (available as APG® 325 CS) and lauryl polyglucoside (available as APG® 600CS and 625 CS), all the above-identified polyglucosides APG® are available from Cognis, Ambler, Pa. Also useful herein are sucrose ester surfactants such as sucrose cocoate and sucrose laurate.

Other nonionic surfactants suitable for use in the present invention are glyceryl esters and polyglyceryl esters, including but not limited to, glyceryl monoesters, preferably glyceryl monoesters of C16-C22 saturated, unsaturated and branched chain fatty acids such as glyceryl oleate, glyceryl monostearate, glyceryl monoisostearate, glyceryl monopalmitate, glyceryl monobehenate, and mixtures thereof, and polyglyceryl esters of C16-C22 saturated, unsaturated and branched chain fatty acids, such as polyglyceryl-4 isostearate, polyglyceryl-3 oleate, polyglyceryl-2 sesquioleate, triglyceryl diisostearate, diglyceryl monooleate, tetraglyceryl monooleate, and mixtures thereof.

Also useful herein as nonionic surfactants are sorbitan esters. Preferable are sorbitan esters of C16-C22 saturated, unsaturated and branched chain fatty acids. Because of the manner in which they are typically manufactured, these sorbitan esters usually comprise mixtures of mono-, di-, tri-, etc. esters. Representative examples of suitable sorbitan esters include sorbitan monooleate (e.g., SPAN® 80), sorbitan sesquioleate (e.g., Arlacel® 83 from ICI Specialty Chemicals, Wilmington, Del.), sorbitan monoisostearate (e.g., CRILL® 6 from Croda, Inc., Edison, N.J.), sorbitan stearates (e.g., SPAN® 60), sorbitan trioleate (e.g., SPAN® 85), sorbitan tristearate (e.g., SPAN® 65), sorbitan dipalmitates (e.g., SPAN® 40), and sorbitan isostearate. Sorbitan monoisostearate and sorbitan sesquioleate are particularly preferred emulsifiers for use in the present invention.

Also suitable for use herein are alkoxylated derivatives of glyceryl esters, sorbitan esters, and alkyl polyglycosides, wherein the alkoxy groups is selected from the group consisting of C2-C6 oxides and their mixtures, with ethoxylated or propoxylated derivatives of these materials being the preferred. Nonlimiting examples of commercially available ethoxylated materials include TWEEN® (ethoxylated sorbitan mono-, di- and/or tri-esters of C12 to C18 fatty acids with an average degree of ethoxylation of from about 2 to about 20).

Preferred nonionic surfactants are those formed from a fatty alcohol, a fatty acid, or a glyceride with a $C_4$ to $C_{36}$ carbon chain, preferably a $C_{12}$ to $C_{18}$ carbon chain, more preferably a $C_{16}$ to $C_{18}$ carbon chain, derivatized to yield an HLB of at least 8. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 8. Preferably the nonionic surfactants contain ethoxylate in a molar content of from 10-25, more preferably from 10-20 moles.

Preferably, the nonionic surfactant(s) is/are present in an amount ranging from about 1% to about 40% by weight of the total weight of the composition, more preferably from about 3% to about 30% of the total weight of the composition, more preferably from about 5% to about 25% of the total weight of the composition, and most preferably from about 10% to about 20%, including all ranges and subranges therebetween. In a preferred embodiment, the amphoteric surfactant(s) and the nonionic surfactant(s) are present in a ratio of from about 1:1 to about 1:2.

Phospholipid Compound

In a particularly preferred embodiment of the present invention, the compositions of the present invention further comprise a phospholipids compound. Most preferably, the phospolipid compound is a lecithin compound. Lecithins are mixtures of phospholipids, i.e., diglycerides of fatty acids linked to an ester of phosphoric acid. Preferably, lecithins are diglycerides of stearic, palmitic, and/or oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids. Any such lecithins can be used in accordance with the present invention. The lecithin compound may be in the form of a liquid, powder, or granules.

Specific examples of acceptable types lecithins include, but are not limited to, soy lecithin and hydroxylated lecithin. Specific lecithin compounds include, but are not limited to, ALCOLEC S which is a fluid soy lecithin, ALCOLEC F 100 which is a powder soy lecithin, and ALCOLEC Z3 which is a hydroxylated lecithin. All of these commercial products are available from the American Lecithin Company.

Also, a group of phospholipids which can be used in the present invention as phospholipids compounds include, but are not limited to, multifunctional biomimetic phospholipids, including, for example, the following multifunctional biomimetic phospholipids manufactured by Mona Industries: PHOSPHOLIPID PTC, PHOSPHOLIPID CDM, PHOSPHOLIPID SV, PHOSPHOLIPID GLA, and PHOSPHOLIPID EFA.

Preferably, the phospholipid compound(s) is/are present in an amount ranging from about 0.01% to about 10% by weight of the total weight of the composition, more preferably from about 0.1% to about 8% of the total weight of the composition, more preferably from about 1% to about 7% of the total weight of the composition, and most preferably from about 3% to about 6%, including all ranges and subranges therebetween. Since phospholipids themselves are not necessarily a pure raw material and may have free glycerides, glycerin, fatty acids, and soaps, adjustments in this amount may need to be made (e.g., one source of lecithin may require slightly different amounts to be present than other amounts to ensure that a sufficient % active material of lecithin compound is present).

When, in accordance with preferred embodiments, a lecithin compound is present, what is sometimes referred to as a "LAN system" or simply as "LAN" (Lecithin, Amphoteric, Nonionic) is present. Such LAN systems have been described in U.S. Pat. No. 6,015,574, U.S. Pat. No. 6,221,389, U.S. Pat. No. 6,524,614, U.S. Pat. No. 6,558,697, and U.S. patent application 2004/0120919, the entire contents of all of which are hereby incorporated by reference.

According to preferred embodiments, the phospholipid compound(s), the amphoteric surfactant(s), and the nonionic surfactant(s) are present such that the nonionic surfactant(s) and the amphoteric surfactant(s) are each present in an amount by weight greater than the amount of phospholipid.

According to other preferred embodiments, calculating the phospholipid as present at a value of 1, the phospholipid compound(s), amphoteric surfactant(s) and nonionic surfactant(s) are preferably present in the composition in a ratio ranging from about 1:0.75:1 to about 1:9:12, more preferably from about 1:1.5:2 to about 1:6:8. Most preferably, the ratio is about 1:3:4.

Preferably, the combined amount of phospholipid compound(s), amphoteric surfactant(s) and nonionic surfactant(s) ranges from about 1% to about 40% by weight of the total weight of the composition, more preferably from about 2% to about 25% of the total weight of the composition, more preferably from about 3% to about 20% of the total weight of the composition, and most preferably from about 4% to about 15%, including all ranges and subranges therebetween.

Additional Ingredients

The compositions of the present invention can also comprise any additive usually used in cosmetic or dermatologic compositions. For example, fibers, waxes, film forming agents, dispersants, antioxidants such as erythorbic acid and salts of sulfites or bisulfites including sodium sulfite, sodium bisulfite, and potassium bisulfite, chelating agents like pentasodium penteate, EDTA and EDTA derivatives thereof like mono-, di, and tri-sodium EDTA, oils, preserving agents such as a paraben (ethyl-, methyl-) or phenoxyethanol, fragrances, pigments, fillers, cationic polymers such as the polyquaternium polymers such as, for example, polyquaternium-6, polyquaternium-22, polyquaternium-24, polyquaternium-37 and polyquaternium-39, neutralizing agents or pH adjusters like hydrochloric acid, phosphoric acid, and ammonium hydroxide, cosmetic and dermatological active agents such as, for example, emollients, humectants such as alkylene glycols like butylene glycol and propylene glycol, moisturizers, vitamins, essential fatty acids, and sunscreens, and mixtures thereof can be added. A non-exhaustive listing of such ingredients can be found in U.S. patent application Ser. No. 10/733,467, filed Dec. 12, 2003, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

Specific examples of additional ingredients also alcohols, particularly if the composition contains an aqueous phase. Any suitable alcohol may be used in accordance with the present invention such as, for example, C2-C5 alcohols like ethanol, propanol, butanol, isopropyl, etc., and mixtures thereof. If present, the alcohol is preferably present in an amount ranging from about 1% to about 80% by weight of the total weight of the composition, more preferably from about 5% to about 60% by weight, and more preferably from about 10% to about 50% by weight.

Specific examples of additional ingredients also include oils, particularly if the composition is an anhydrous composition or an emulsion. Any oils can be used in accordance with the present invention. The oils can be volatile or non-volatile, silicone-based and/or hydrocarbon-based, etc. Thus, for example, the external oil phase may contain, independently or in combination, volatile silicone oils, non-volatile silicone oils, volatile non-silicone oils and non-volatile non-silicone oils.

In one embodiment, the compositions of the present invention are substantially free of silicone oils (i.e., contain less than about 1% of silicone oil). In another embodiment, the compositions are substantially free of non-silicone oils (i.e., contain less than about 1% of non-silicone oil). In another embodiment, the compositions are substantially free of non-volatile oils (i.e., contain less than about 1% of non-volatile oil). In yet another embodiment, the compositions are substantially free of volatile oils (i.e., contain less than about 1% of volatile oil).

Water, when present, preferably represents from about 1% to about 70% by weight of the total weight of the composition, more preferably from about 5% to about 60% of the total weight of the composition, and most preferably from about 10% to about 50%, including all ranges and subranges therebetween.

The compositions may also optionally comprise at least one oxidation dye chosen from oxidation bases and oxidation couplers. In one embodiment, the compositions can comprise at least one oxidation base. Suitable oxidation bases include those conventionally known as oxidation dyes. Representative oxidation dyes include ortho- and para-phenylenediamines, double bases, ortho- and para-aminophenols and heterocyclic bases as well as their addition salts with an acid such as those described in U.S. patent application publication No. 2002/0013972, the entire contents of which is hereby incorporated by reference.

Among the para-phenylenediamines, mention may be made of para-phenylenediamine, 2-methyl-para-phenylenediamine, 1-(N-ethyl-N'-β-hydroxyethyl)-amino-4-aminobenzene, 1-N,N'-bis(β-hydroxyethyl)amino-4-aminobenzene, 1-N,N'-bis(β,γ-dihydroxypropyl)amino-4-aminobenzene, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, 2-methyl-5-methoxy-para-phenylenediamine, 2,6-dimethyl-5-methoxy-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, 4-amino-N,N-diethyl-2-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 4-amino-N-ethyl-N-carbamylmethylaniline, 4-amino-3-methyl-N-ethyl-N-carbamylmethylaniline, 4-amino-N-ethyl-N-(β-piperidinoethyl)aniline, 4-amino-3-methyl-N-ethyl-N-(β-piperidinoethyl) aniline, 4-amino-N-ethyl-N-(β-morpholinoethyl)aniline, 4-amino-3-methyl-N-ethyl-N-(β-morpholinoethyl)aniline, 4-amino-ethyl-N-(β-acetylaminoethyl)aniline, 4-amino-N-(β-methoxyethyl)aniline, 4-amino-3-methyl-N-ethyl-N-(β-acetylaminoethyl)aniline, 4-amino-N-ethyl-N-(β-mesylaminoethyl)aniline, 4-amino-3-methyl-N-ethyl-N-(β-mesylaminoethyl) aniline, 4-amino-N-ethyl-N-(β-sulphoethyl)aniline, 4-amino-3-methyl-N-ethyl-N-(β-sulphoethyl)aniline, N-[4'-(amino)phenyl]morpholine, N[4'-(amino)phenyl]piperidine, N-(4'-aminophenyl)-para-phenylenediamine, N-phenyl-para-phenylenediamine, 2-fluoro-para-phenylenediamine, 2-carboxy-para-phenylenediamine, 2-sulpho-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, 2-β-hydroxyethyloxy-para-phenylenediamine, 2-β-acetylaminoethyloxy-para-phenylenediamine, N-β-methoxyethyl-para-phenylenediamine, para-toluylenediamine, 2-n-propyl-para-phenylenediamine, 1,β-methoxyethylamino-4-aminobenzene, 4-aminophenyl 1-(3-hydroxy)pyrrolidone, and acid addition salts thereof.

Among the ortho-phenylenediamines, mention may be made of 4-Methyl-o-Phenylenediamine, and acid addition salts thereof. As used herein, the term double bases means compounds comprising at least two aromatic nuclei having at least one of amino and hydroxyl groups.

Among the double bases that can be used as oxidation bases in the dye compositions disclosed herein, mention may be made of amino, mono($C_1$-$C_4$)alkylamino, di($C_1$-$C_4$)alkylamino, tri($C_1$-$C_4$) alkylamino, monohydroxy($C_1$-$C_4$)alkylamino, imidazolinium, and ammonium radicals. Mention may also be made of N,N'-bis-(β-hydroxyethyl)-N,N'-bis(4'-aminophenyl)-1,3-diaminopropanol, N,N'-bis(β-hydroxyethyl)-N,N'-bis(4'-aminophenyl) ethylenediamine, N,N'-bis(4-aminophenyl)tetra-methylenediamine, N,N'-bis(β-hydroxyethyl)-N,N'-bis-(4-aminophenyl) tetramethylenediamine, N,N'-bis(4-methylaminophenyl) tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the acid addition salts thereof.

Among the para-aminophenols, mention may be made of para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(β-hydroxyethylaminomethyl)phenol, N-methyl-para-aminophenol, and the acid addition salts thereof.

The ortho-aminophenols that may be used as oxidation bases in the context of certain embodiments may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Among the heterocyclic bases that can be used as oxidation bases in the dye compositions in accordance with certain embodiments, mention may be made of pyridine derivatives, pyrimidine derivatives, pyrazole derivatives, pyrazolinone derivatives, and the acid addition salts thereof.

Among the pyridine derivatives, mention may be made of the compounds described, for example, in patents GB 1,026,978 and GB 1,153,196, as well as the compounds 2,5-diaminopyridine, 2-(4-methoxyphenyl)amino-3-aminopyridine, 2,3-diamino-6-methoxypyridine, 2-(β-methoxyethyl)amino-3-amino-6 methoxypyridine, 3,4-diaminopyridine, and the acid addition salts thereof.

Among the pyrazole and pyrazolinone derivatives, mention may be made the compounds described in patents DE 3,843,892, DE 4,133,957 and patent applications WO 94/08969, WO 94/08970, FR-A-2,733,749, and DE 195 43 988, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, 2-(4,5-diamino-1H-pyrazol-1-yl), and the acid addition salts thereof.

The oxidation bases, if present, may be employed in amounts ranging from 0.0001% to 12% by weight; from 0.001% to 8% by weight, all weights being based on the total weight of the composition.

The couplers that may be used in the dyeing method disclosed herein include those conventionally used in oxidation dye compositions, that is to say meta-aminophenols, meta-phenylenediamines and meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, and the acid addition salts thereof.

These couplers may be chosen, for example, from 2,4-diamino-1-(β-hydroxyethyloxy)benzene, 2-methyl-5-aminophenol, 5-N-(β-hydroxyethyl) amino-2-methylphenol, 3-aminophenol, 1,3-dihydroxybenzene, 1,3-dihydroxy-2-methylbenzene, 4-chloro-1,3-dihydroxybenzene, 2,4-diamino 1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole, 2,6-dimethylpyrazolo[1,5-b]-1,2,4-triazole, 6-methylpyrazolo[1,5-a]-benzimidazole, and the acid addition salts thereof.

When they are present, these couplers may be present in amounts ranging from 0.0001% to 12% by weight; from 0.001% to 8% by weight, all weights being based on the total weight of the composition. In general, the acid addition salts of the oxidation bases and couplers may be chosen from hydrochlorides, hydrobromides, sulphates, tartrates, lactates, and acetates.

The composition disclosed herein may also comprise at least one direct dye, in addition to the at least one oxidation dye defined above, in order to enrich the shades with glints. This at least one direct dye may be chosen from neutral, cationic, and anionic nitro dyes, azo dyes, and anthraquinone dyes, and may be present in amounts ranging from 0.001% to 20% by weight; from 0.01% to 10% by weight, all weights being based on the total weight of the composition.

According to preferred embodiments of the present invention, methods of methods of conditioning, strengthening and/or disentangling hair comprising applying a composition comprising Ionene G, at least one amphoteric surfactant and at least one nonionic surfactant to the hair in an amount sufficient to condition, strengthen and/or disentangle the hair are provided. In accordance with particularly preferred embodiments of the present invention, methods of methods of conditioning, strengthening and/or disentangling hair comprising applying a composition comprising Ionene G, at least one amphoteric surfactant, at least one nonionic surfactant and at least one phospholipid compound to the hair in an amount sufficient to condition, strengthen and/or disentangle the hair are provided.

According to still other embodiments of the present invention, methods of treating, caring for, coloring or enhancing the appearance of keratin materials comprising applying compositions of the present invention to the keratin materials in an amount sufficient to treat, care for, color and/or enhance the appearance of the keratin materials are provided.

In accordance with the foregoing embodiments of the present invention, the compositions of the present invention may be applied to keratin materials as needed, preferably once or twice daily, more preferably once daily.

According to other preferred embodiments of the present invention, methods of stabilizing Ionene G comprising combining Ionene G with at least one amphoteric surfactant and at least one nonionic surfactant are provided. According to particularly preferred embodiments, Ionene G is stabilized with at least one amphoteric surfactant, at least one nonionic surfactant and at least one phospholipid compound. In accordance with a particularly preferred embodiment, the phospholipid is a lecithin compound and the LAN system is present in an amount sufficient to stabilize Ionene G, preferably for at least 2 months at 45° C., more preferably for at least 3 months at 45° C.

According to yet other embodiments of the present invention, methods of producing a composition comprising Ionene G comprising combining Ionene G with at least one amphoteric surfactant and at least one nonionic surfactant are provided. Preferably, Ionene G is also combined with a phospholipid compound (for example, Ionene G is combined with a LAN system) to produce a composition.

The present invention also envisages kits and/or prepackaged materials suitable for consumer use containing one or more compositions according to the description herein (for example, kits containing (1) a shampoo composition or a hair coloring composition; and (2) a conditioner, either leave-in or rinse-out). Such kits may also include other compositions or components such as, for example, instructions for applying or using the compositions in the kit, cosmetic application devices (for example, a hair brush), etc.

The packaging and application device for any subject of the invention may be chosen and manufactured by persons skilled in the art on the basis of their general knowledge, and adapted according to the nature of the composition to be packaged. Indeed, the type of device to be used can be in particular linked to the consistency of the composition, in particular to its viscosity; it can also depend on the nature of the constituents present in the composition, such as the presence of volatile compounds.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLE 1

Formulations

The following base formulations A and B were used to prepare compositions.

| INGREDIENT | % WEIGHT |
|---|---|
| Base Formula A | |
| COCAMIDE MIPA | 8.0 |
| ETHYL LINOLEATE | 11.0 |
| ISOPROPYL ALCOHOL | 10.0 |
| PROPYLENE GLYCOL | 7.0 |
| PPG-2 BUTYL ETHER | 5.0 |
| DECETH-3 | 9.0 |
| SODIUM C14-16 OLETH SULFONATE | 22.5 |
| PPG-5-CETETH-10 PHOSPHATE | 0.9 |
| COCO-BETAINE | 2.0 |
| CHELATING AGENT | 0.2 |
| PEG/PPG-4/12 DIMETHICONE | 1.5 |
| LAN SYSTEM 1 | 0.2 |
| TOTAL BASE A | 77.3 |
| Base Formula B | |
| ANTIOXIDANTS | 1.0 |
| FRAGRANCE | 0.7 |
| PH ADJUSTER | 7.8 |
| WATER | 13.2 |

-continued

| INGREDIENT | % WEIGHT |
|---|---|
| TOTAL BASE B | 22.7 |
| TOTAL BASE A + B | 100.0 |

To these formulations, mixtures containing surfactants and Ionene G were added. Ionene G was in aqueous solution (60% active material). One standardized surfactant system used was LAN System 1, which is described in the following table.

| INCI NAME | % WEIGHT |
|---|---|
| LAN System 1 | |
| PRESERVATIVES | 0.6 |
| CHELATING AGENT | 0.1 |
| NONIONIC SURFACTANT | 23.0 |
| 2-OLEAMIDO-1,3-OCTADECANEDIOL | 1.0 |
| AMPHOTERIC SURFACTANT | 7.6 |
| PH ADJUSTER | 1.2 |
| WATER | QS100 |
| PHOSPHOLIPID | 4.0 |
| PRESERVATIVES | 0.2 |
| Total | 100.0 |
| LAN System 2 | |
| NONIONIC SURFACTANT | 20.0 |
| AMPHOTERIC SURFACTANT | 15.0 |
| WATER | QS100 |
| PHOSPHOLIPID | 5.0 |
| Total | 100.0 |

Using these base formulations, the following compositions were prepared and tested for stability at 45° C. for at least 2 months. "Pass" indicates that the compositions were stable. "Fail" indicates that the compositions were not stable.

| Example | LAN + Ionene G (60% Ionene G in 40% water)) | | Ionene G (active amount) | Results (stability at 45° C.) |
|---|---|---|---|---|
| 1 | 10% Lecithin 30% Amphoteric 40% Nonionic 20% Ionene G (with water) | 4% LAN + Ionene G 96% Base A & B | 0.48% | pass |
| 2 | 10% Lecithin 30% Amphoteric 40% Nonionic 20% Ionene G (with water) | 4% LAN + Ionene G 96% Base A & B | 0.48% | pass |
| 3 | 92.5% LAN System 1 7.5% Ionene G (with water) | 12% LAN + Ionene G 88% Base A & B | 0.54% | Pass (light material on bottle bottom) |
| 4 | 85% LAN System 1 15% Ionene G (with water) | 6% LAN + Ionene G 94% Base A & B | 0.54% | pass |
| 5 | 30% Amphoteric 40% Nonionic 30% Ionene G (with water) | 4% LAN + Ionene G 96% Base A & B | 0.72% | pass |
| 6 | 5% Lecithin 15% Amphoteric 20% Nonionic 50% Water 10% Ionene G (with water) | 12% LAN + Ionene G 88% Base A & B | 0.72% | pass |
| 7 | 80% LAN System 1 20% Ionene G (with water) | 6% LAN + Ionene G 94% Base A & B | 0.72% | pass |
| 8 | 75% LAN System 1 25% Ionene G (with water) | 6% LAN + Ionene G 94% Base A & B | 0.90% | fail |
| 9 | 10% Lecithin 30% Amphoteric 40% Nonionic 20% Ionene G (with water) | 8% LAN + Ionene G 92% Base A & B | 0.96% | fail |
| 10 | 70% LAN System 1 30% Ionene G (with water) | 6% LAN + Ionene G 94% Base A & B | 1.08% | fail |
| 11 | 85% LAN System 1 15% Ionene G (with water) | 12% LAN + Ionene G 88% Base A & B | 1.08% | Pass (light material on bottle bottom) |
| 12 | 3.5% Lecithin 10.5% Amphoteric 14% Nonionic 42% Water 30% Ionene G (with water) | 6% LAN + Ionene G 94% Base A & B | 1.08% | fail |
| 13 | 85% LAN System 1 15% Ionene G (with water) | 12% LAN + Ionene G 88% Base A & B | 1.08% | pass |
| 14 | 10% Lecithin 30% Amphoteric 40% Nonionic 20% Ionene G (with water) | 12% LAN + Ionene G 88% Base A & B | 1.44% | fail |
| 15 | 80% LAN System 1 20% Ionene G (with water) | 12% LAN + Ionene G 88% Base A & B | 1.44% | fail |
| 16 | 75% LAN System 1 25% Ionene G (with water) | 12% LAN + Ionene G 88% Base A & B | 1.80% | fail |
| 17 | 70% LAN System 1 30% Ionene G (with water) | 12% LAN + Ionene G 88% Base A & B | 2.16% | fail |
| 18 | 3.5% Lecithin 10.5% Amphoteric 14% Nonionic 42% Water 30% Ionene G (with water) | 12% LAN + Ionene G 88% Base A & B | 2.16% | fail |

What is claimed is:

1. A method of conditioning hair comprising applying a composition comprising:
   a) at least one C2-C5 alcohol present in an amount of 1% to 80% by weight of the total weight of the composition;
   b) at least one alcohol-insoluble quaternary ammonium polymer;
   c) at least one amphoteric surfactant;
   d) at least one nonionic surfactant, and
   e) at least one phospholipid compound,
   wherein the at least one alcohol-insoluble quaternary ammonium polymer and the amphoteric surfactant(s) are present in a ratio of from about 1:1 to about 1:2 and wherein the amphoteric surfactant(s) and the nonionic surfactant(s) are present in a ratio of from about 1:1 to about 1:2, to hair in an amount sufficient to condition the hair.

2. The method according to claim 1, wherein the alcohol-insoluble quaternary ammonium polymer comprises polyquaternium-34.

3. The method according to claim 1 wherein the alcohol-insoluble quaternary ammonium polymer comprises hexadimethrine chloride.

4. The method according to claim 1, wherein the combined amount of phospholipid compound(s), amphoteric surfactant(s) and nonionic surfactant(s) in the composition ranges from about 3% to about 20% by weight with respect to the total weight of the composition.

5. The method according to claim 1, wherein the combined amount of phospholipids compound(s), amphoteric surfactant(s) and nonionic surfactant(s) in the composition ranges from about 4% to about 15% by weight with respect to the total weight of the composition.

6. The method according to claim 1, wherein the composition further comprises at least one oxidation dye.

7. The method according to claim 1, wherein the amount of alcohol-insoluble quaternary ammonium polymer present in the composition ranges from about 0.4% to about 1.25% by weight with respect to the total weight of the composition.

8. The method according to claim 1, wherein the amount of alcohol-insoluble quaternary ammonium polymer present in the composition ranges from about 0.8% to about 1.2% by weight with respect to the total weight of the composition.

9. The method according to claim 1, wherein the phospholipid comprises a lecithin compound.

10. The method according to claim 1, wherein the C2-C5 alcohol is present in an amount of 5% to 60% by weight of the total weight of the composition.

\* \* \* \* \*